United States Patent [19]

Vignau

[11] 3,941,811

[45] Mar. 2, 1976

[54] OXIDATION PROCESS
[75] Inventor: Michel Vignau, Neuilly-sur-Seine, France
[73] Assignee: Roussel-UCLAF, Paris, France
[22] Filed: Feb. 11, 1974
[21] Appl. No.: 440,984

Related U.S. Application Data
[63] Continuation of Ser. No. 265,522, June 23, 1972, abandoned.

[30] Foreign Application Priority Data
July 1, 1971 France .............................. 71.24086

[52] U.S. Cl........... 260/335; 260/396 R; 260/397.3; 260/397.4; 260/340.5; 260/591; 260/586 P; 260/596
[51] Int. Cl.² ................. C07D 311/86; C07C 49/64; C07C 49/66; C07C 45/16
[58] Field of Search............. 260/335, 396 R, 340.5, 260/397.3, 397.4, 591, 586 P, 596

[56] References Cited
UNITED STATES PATENTS
1,813,953  7/1931  Reppe................................ 260/596
3,080,426  3/1963  Kirshenbaum et al. ......... 260/586 B FOREIGN PATENTS OR APPLICATIONS
976,729  3/1964  Germany......................... 260/596 R

OTHER PUBLICATIONS

Chemical Abstracts, Vol. 57, 15863c.

Chemical Abstracts, Vol. 59, 3345h.

Fieser et al., Reagents for Organic Synthesis (1969) p. 363.

Primary Examiner—Norma S. Milestone
Attorney, Agent, or Firm—Hammond & Littell

[57] ABSTRACT

A novel liquid phase oxidation process using silver silicate as the oxidizing agent which is particularly adapted for oxidation of a hydroxy attached to a carbon atom to a carbonyl group.

7 Claims, No Drawings

OXIDATION PROCESS

PRIOR APPLICATION

This application is a continuation of U.S. patent application Ser. No. 265,522 filed June 23, 1972, now abandoned.

STATE OF THE ART

The oxidation of certain hydroxy groups to carbonyl groups with the use of silver salts has been described in the literature. For example, Syper [Tetra. Let., Vol. 42 (1967), p. 4193] describes the use of silver oxide, Rapoport et al. [J.A.C.S., Vol. 77 (1955), p. 490] and King et al. [J. Org. Chem., Vol. 26, (1961), p. 3558] describe the use of silver carbonate, Fetizon et al. [C.R. Acad. Sc. Paris, Vol. 267, Series C 900 and Dutch patent application No. 6,811,843] describe the use of silver carbonate disposed on celite, and Lee at al. [Tetra. Let., No. 5 (1967), p. 415] and Clarke [Can. J., Vol. 47 (1969), p. 1650] describe the use of silver α-picolinate.

A process for the vapor phase dehydrogenation of methanol in formol using a catalyst prepared by starting from silver silicate has been described but in fact, the said catalyst is obtained by hydrogenation of silver silicate at 250°C and it, in reality, constitutes reduced silver disposed on silica. Moreover, the said reduction is effected in the vapor phase and not the liquid phase.

OBJECTS OF THE INVENTION

It is an object of the invention to provide a novel liquid phase oxidation process using silver silicate as the oxidizing agent.

It is a further object of the invention to provide an improved process to oxidize a hydroxy attached to a carbon atom to a carbonyl in high yields.

These and other objects and advantages of the invention will become obvious from the following detailed description.

THE INVENTION

The novel process of the invention comprises oxidizing in the liquid phase a hydroxy attached to a carbon atom to a carbonyl group using silver silicate as the oxidizing agent. The oxidation is preferably effected in a non-hydroxylated organic solvent such as ethyl acetate, benzene, cyclopentane, toluene, acetone, dichloroethane, etc.

To effect the oxidation, it is preferable to use 1.5 to 3.5 times the theoretical amount of silver silicate, that is a molecule/gram of silver silicate per mole of hydroxy compound.

The practical method of effecting the oxidation comprises contacting the hydroxy compound, the silver silicate and the organic solvent heating the resulting mixture to reflux, filtering the mixture to remove excess silver silicate, eliminating volatile fraction and then eventually purifing the residue by the usual known physical methods.

The reaction is advantageously effected in the presence of a dehydrating agent in the solvent used such as sillporite (dehydrated alkali metal aluminium silicates) or by removal of the water formed by azeotropic distillation.

Primary alcohols are oxidized to aldehydes and the reaction does not continue to the acid stage and secondary alcohols are oxidized to ketones. Tertiary alcohols are not attacked while diphenols are oxidized to the corresponding quinones. The yields of the process of the invention are high, on the order of 90% and in some cases, practically theoretical yields are obtained. The process has the advantage of giving very high yields as compared to known processes with other silver salts.

The process of the invention has the advantage over silver carbonate as being useful for the oxidation of a large variety of alcohols or diphenols while silver carbonate has been used only for the oxidation of codeine into codeinone and in being able to obtain very high yields.

With respect to the prior art process using silver carbonate on celite, the process of the invention has the advantage that it requires only a small amount of reagent (1.5 to 3.5 times theoretical) while the prior art process requires the use of more reagent, about 8 to 15 times that of theory and an equally large amount of celite. This permits the process of the invention to cost substantially less and to use a greatly reduced amount of solvent. Moreover, the silver carbonate had to be specially prepared while the silver silicate used in the process of the invention is a commercial product.

Moreover, in certain cases, the process of the invention is more effective than the process using silver carbonate on celite. For example, the process of the invention permits oxidation of 3-O-methyloximino-$\Delta^{4,9}$-estradiene-17-ol to 3-O-methyloximino-$\Delta^{4,9}$-estradiene-17-one while the process with silver carbonate on celite will not give the desired result.

With respect to the prior art process using silver picolinate, the process of the invention has the advantage of giving much higher yields, of not using a costly reagent, commercial availability and possesses the further advantage of containing for the same weight a quantity of active silver clearly much higher than that for silver picolinate.

With respect to the use of other silver salts, silver silicate has the advantage of not presenting ageing. In other words, the rate of oxidation with silver silicate is always constant and regular while with other reagents such as silver carbonate on celite, the rate of oxidation diminishes as a function of time and especially the time of increased latency with the age of the reagent.

The alcohols oxidized by the process of the invention may be primary and secondary alcohols of a diverse nature. They may be aliphatic, cycloaliphatic, aromatic or heterocyclic. Examples of suitable alcohols are aliphatic and arylaliphatic alcohols of 1 to 18 carbon atoms such as 3,4-methylenedioxybenzyl alcohol; cycloalkanols of 5 to 8 ring carbons such as cyclohexanols etc.; heterocyclic alcohols such as 9-hydroxy-xanthene; aromatic alcohols such as hydroquinone, naphthalene-1,4-diol, 2-methyl-1,4-dihydroxynaphthalene, etc; steroid alcohols such as 3-methoxy-$\Delta^{1,3,5}$-estratriene-17ol, 3-hydroxy-cholestane, 3α-hydroxy-5-β-androstane, 3-hydroxy-5α-pregnane-20-one, etc.

In summary, the process of the invention has the advantage of oxidizing the hydroxy group without regard to other reactive functions in the compound; the yields are very high; the applicability of the process is great; the process is simple particularly in the method of recovering the product; the reagent used, silver silicate, is stable, commerically available and inexpensive to prepare; it uses a small excess of reagent; and it permits oxidation in a neutral media.

In the following examples there are described several preferred embodiments to illustrate the invention. However, it should be understood that the invention is not intended to be limited to the specific embodiments.

EXAMPLE I

Preparation of Silver Silicate

A solution of 75 g of sodium silicate pentahydrate in 1500 ml of water was introduced with stirring in the absence of air and light into a solution of 100 g of silver nitrate in 500 ml of distilled water and after stirring for 30 minutes, the mixture was allowed to stand for an hour. The precipitate formed was recovered by vacuum filtration and was washed with water and dried in the presence of a dehydrating agent to obtain 80 g of silver silicate ($Ag_2SiO_3$). Analysis showed a silver content of 72.6% (theoretical —73.93) and a $SiO_2$ content of 20.3% (theoretical 20.6).

A commerical silver silicate sold by Engelhard gave in the oxidation of hydroxyl groups the same results as the above prepared silver silicate.

EXAMPLE II 198.2 g of 9-hydroxy-xanthane, 30 ml of cyclopentane and 500 mg of silver silicate were introduced into a flask supplied with a refridgerant of which the base was filled with siliporite (dehydrated alkali metal aluminum silicates) and the mixture was refluxed for 40 minutes. The mixture was then filtered and the filtrate was concentrated to dryness by distillation under reduced pressure to obtain 196 mg of 9-oxoxanthene melting at 174°C.

EXAMPLE III

272 Mg of 1-oxo-1,2-bis-p-methoxy-phenyl-2-hydroxyethane, 600 mg of silver silicate and 30 ml of benzene were added to a flask as described in Example II and the mixture was refluxed for 4 hours. The mixture was then filtered and the filtrate was concentrated to dryness by distillation under reduced pressure to obtain 254 mg of 1,2-dioxo-1,2-bis-p-methoxyphenyl-ethane melting at 132°C.

In an analogous manner, 1-oxo-1,2-bis-phenyl-2-hydroxyethane was oxidized to obtain an 84% yield of 1,2-dioxo-1,2-bis-phenyl-ethane.

EXAMPLE IV

152 Mg of 3,4-methylenedioxy-benzyl alcohol, 500 mg of silver silicate and 30 ml of benzene were added to the flask described in Example II and the mixture was refluxed for 45 minutes and was then filtered to obtain 139 mg of 3,4-methylenedioxy-benzaldehyde melting at 36.8°C.

EXAMPLE V

110 Mg of hydroquinone, 500 mg of silver silicate and 30 ml of benzene were added to the flask of Example II and the mixture was refluxed for 15 minutes. The mixture was filtered and the filtrate was distilled to dryness under reduced pressure to obtain 95 mg of benzoquinone melting at 114°C.

Using the same procedure, napthalene-1,4-diol and 1,4-dihydroxy-2-methyl-naphthalene were oxidized to obtain a 93% yield of 1,4-naphthoquinone and a 97% yield of 2-methyl-1,4-naphthoquinone, respectively.

EXAMPLE VI

286 Mg of 3-methoxy-$\Delta^{1,3,5}$-estratriene-17-ol, 600 mg of silver silicate and 30 ml of benzene were added to the flask of Example II and the mixture was refluxed 1¾ hours. Another 150 mg of silver silicate were added thereto and the mixture was refluxed for another 1½ hours. The mixture was then filtered and the filtrate was distilled to dryness under reduced pressure to obtain 281 mg of 3-methoxy-$\Delta^{1,3,5}$-estratriene-17-one melting at 170°C.

EXAMPLE VII 388.6 Mg of 3-hydroxy-cholestane, 500 mg of silver silicate and 30 ml of ethyl acetate were added to the flask of Example II and the reaction mixture was refluxed for 10 hours. Another 50 mg of silver silicate were added thereto and reflux was continued for 5 hours. The mixture was then filtered and the filtrate was concentrated to dryness. The residue was dissolved in ether and the ether was distilled off under reduced pressure to obtain 383 mg of cholestane-3-one melting at 115°C, then 128°C.

Using the same process, 5$\beta$-androstane-3$\alpha$-ol and 5$\alpha$-pregnane-3-ol-20-one were oxidized to obtain a 98.8% yield of 5$\beta$-androstane-3-one and a 94.3% yield of 5$\alpha$-pregnane-3,20-dione respectively.

Various modifications of the process of the invention may be made without departing from the spirit or scope thereof and it should be understood that the invention is to be limited only as defined in the appended claims.

I claim:

1. In a liquid phase oxidation of compounds containing a hydroxy attached to a carbon atom into the corresponding carbonyl compound, the improvement which comprises using silver silicate having the empirical formula $Ag_2SiO_3$ as the oxidizing agent.

2. The process of claim 1 wherein the reaction is effected in a non-hydroxylated organic solvent.

3. The process of claim 1 wherein the amount of silver silicate used is 1.5 to 3.5 times the theoretical amount.

4. The process of claim 2 wherein the reaction is effected at reflux temperatures.

5. A liquid phase oxidation comprising refluxing a mixture of silver silicate having the formula $Ag_2SiO_3$ and a compound containing a hydroxyl attached to a carbon atom in a nonhydroxylated organic solvent to oxidize the said hydroxyl group to a carbonyl group while removing the water of reaction formed and recovering the said carbonyl compound, the amount of silicate being 1.5 to 3.5 times the theoretical amount.

6. The process of claim 1 wherein the hydroxy containing compound is an aromatic compound having two phenolic functions.

7. The process of claim 1 wherein the compound containing a hydroxy attached to a carbon atom is 9-hydroxy-xanthene.

* * * * *